United States Patent

Daneshtalab et al.

Patent Number: 5,120,750
Date of Patent: Jun. 9, 1992

[54] GENERATION OF 1,4-DIHYDROPYRIDINE DERIVATIVES

[75] Inventors: Mohsen Daneshtalab; Dai Q. Nguyen, both of Edmonton; Ronald G. Micetich, Sherwood Park, all of Canada

[73] Assignee: SynPhar Laboratories, Inc., Edmonton, Canada

[21] Appl. No.: 508,612

[22] Filed: Apr. 11, 1990

Related U.S. Application Data

[63] Continuation-in-part of Ser. No. 308,923, Feb. 13, 1989, abandoned.

[51] Int. Cl.⁵ .............. A61K 31/44; C07D 401/12
[52] U.S. Cl. .............. 514/340; 514/341; 514/342; 546/275; 546/279; 546/280
[58] Field of Search .............. 546/275, 279, 280; 514/340, 341, 342

[56] References Cited

U.S. PATENT DOCUMENTS 4,418,197  11/1983  Kamibayashi et al. .............. 546/279
4,419,518  12/1983  Kamibayashi et al. .............. 546/279

FOREIGN PATENT DOCUMENTS 140989  11/1981  Japan .
226876  10/1985  Japan .

OTHER PUBLICATIONS

CA 102:113481a.

Primary Examiner—Jane T. Fan
Attorney, Agent, or Firm—Nikaido, Marmelstein, Murray & Oram

[57] ABSTRACT

A 1,4-dihydropyridine derivative of the formula I:

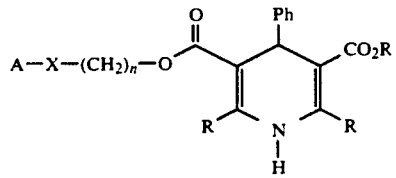

is provided in which:
A is an azole moiety;
R is a $C_1$-$C_4$ alkyl group;
X is —$CH_2$—, —S—, —SO— or —$SO_2$—;
n is 5, 6, 7 or 8; and
Ph is a phenyl group substituted once or twice by $NO_2$, $CF_3$ or Cl groups.

65 Claims, No Drawings

GENERATION OF 1,4-DIHYDROPYRIDINE DERIVATIVES

CROSS-REFERENCE TO RELATED APPLICATION

This application is a continuation-in-part of my application for U.S. Letter Patent Ser. No. 07/308,923, filed Feb. 13, 1989, now abandoned.

FIELD OF THE INVENTION

The present invention relates to novel 1,4-dihydropyridine compounds, to processes for their preparation and to their use primarily as cardiovascular regulating agents.

BACKGROUND OF THE INVENTION

It is well known that numerous 1,4-dihydropyridine derivatives exhibit calcium channel blocking (or antagonist) antihypertensive activity.

Exemplary compounds of this type have been described in Japanese Patent 60,226,876 [85,226,876](11, 1985); Japanese Patent 5978,185 [8478, 185](5, 1984); Japanese Patent 6097,955 [8597, 955](5, 1985); French Patent 2,511,370 (3, 1983) and EP 151,006 [8, 1985).

Of particular interest is the disclosure of D. J. Tiggle et al. entitled "Dimeric 1,4-Dihydropyridines as Calcium Channel Antagonists" in J. Med. Chem. 1988, 31, 1489-1492.

SUMMARY OF THE INVENTION

The invention comprises a 1,4-dihydropyridine derivative of the formula I:

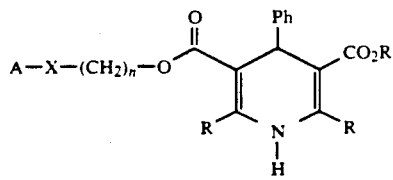

I in which:
A is an azole moiety, by an azole moiety is meant an aromatic five-membered heterocyclic ring having one or two heteratoms such as oxygen, nitrogen or sulphur. The azole moiety may be optionally substituted by a halogen group, or a $C_1$-$C_4$ alkyl group. Preferably, the optional substituent would be selected from a $CH_3$ group, or $CO_2R$ group, wherein R is a $C_1$-$C_4$ alkyl group, or a CN group or a $NO_2$ group;
R is, more specifically, a $C_1$-$C_4$ alkyl group;
X is $-CH_2-$, $-S-$, $-SO-$ or $-SO_2-$;
n is 5, 6, 7 or 8; and
Ph is a phenyl group substituted once or twice by $NO_2$, $CF_3$ or Cl groups.

In a first preferred embodiment there is provided a 1,4,dihydropyridine derivative of the formula II:

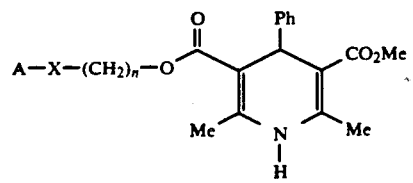

II wherein:
A is 3-methyl-5-isoxazolyl; 3,5-dimethyl-1-pyrazolyl, or 4-methyl-2-thiazolyl;
X is a $-CH_2-$, $-S-$, $-SO-$ or $-SO_2$;
n is 5, 6, 7 or 8; and
Ph is a phenyl group substituted once or twice by $NO_2$, $CF_3$, or Cl groups.

In a second preferred embodiment, the pharmaceutical compound has the structural formula II in which A is 4-methyl-2-thiazolyl; X is methylene; n is 6; and Ph is a phenyl group substituted once by $NO_2$.

In a third preferred embodiment the pharmaceutical compound has a structural formula II wherein A is 3-methyl-5-isoxazolyl; X is methylene; n is 6; and Ph is a phenyl group substituted once by $NO_2$.

In a fourth preferred embodiment, the pharmaceutical compound has the structural formula II wherein A is 4-methyl-2-thiazolyl; X is sulfone; n is 6; and Ph is a phenyl group substituted once by $NO_2$.

It has been found that physiologically acceptable compounds of the formulae I and II possess valuable pharmacological properties. More particularly, they exhibit specific calcium channel blocking activity. Advantageously, such compounds exhibit no effect, or in some instances, positive ionotropic effect on the heart muscle without altering the heart rate and produce a relaxation effect on smooth muscle.

Furthermore, it has been discovered that such compounds exhibit angiotensin inhibitory activity in addition to their calcium channel blocking activity. That such compounds possess both of these properties together is not only most beneficial but also somewhat surprising because the controlling mechanisms for angiotensin inhibition and high blood pressure control are different.

Also these compounds exhibit BradyKinine inhibitory, anti-inflammatory, and an anti-ulcer stressic effects.

Thus, the compounds of the formulae I and II can be used as active compounds in medicaments.

The compounds of formulae I and II can have an asymmetric carbon at the C4 position of the 1,4-dihydropyridine ring. Thus they can exist as racemates in various optically active forms.

In another aspect of the invention, there is provided a process for the preparation of the compounds of the formulae I and II. The process is characterized in that an aromatic five-membered heterocyclic alkyl acetoacetate, of the general formula III:

$$R_3-(CH_2)_n-O-CO-CH_2-CO-CH_3 \qquad III$$

in which $R_3$ is 3-methyl-5-isoxazolyl, 3,5-dimethyl-1-pyrazolyl, or 4-methyl-2-thiazolyl and n has a value of between 5 to 8, is reacted with methyl-$\beta$-aminocrotonate and a mono or disubstituted benzaldehyde of the general formula IV:

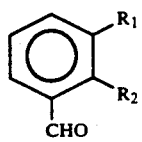

IV in which $R_1$ is a hydrogen, nitro, trifluoromethyl or chloro, $R_2$ is a hydrogen, nitro, trifluoromethyl or chloro, or $R_1 = R_2$ and is a chloro group. The reaction is carried out in a suitable solvent.

The compounds of the general formula III may be prepared by reacting diketene, in an inert solvent, with a substituted aromatic five-membered heterocyclic ω-alkanol having the general formula V:

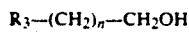

$$R_3-(CH_2)_n-CH_2OH \quad\quad V$$

in which $R_3$ is 3-methyl-5-isoxazolyl, 3,5-dimethyl-1-pyrazolyl or 4-methyl-2-thiazolyl and n has a value of between 4 to 7.

The compounds having the general formula V may be prepared by reacting the appropriate lithium salt of the 3,5-dimethyl isoxazole, 3,5-dimethylpyrazole or 2,4-dimethyl thiazole with 6-bromo-1-hexanol in an inert solvent, preferably at a temperature in the range of about $-70°$ C.

The compounds having the general formula I and II, wherein X comprises sulfur, sulfoxide or sulfone, may be prepared by reacting a substituted aromatic five-membered heterocyclic mercapto, sulfoxy, or sulfonyl alkyl acetoacetate having the general formula VI:

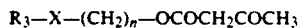

$$R_3-X-(CH_2)_n-OCOCH_2COCH_3 \quad\quad VI$$

in which $R_3$ is 4-methyl-2-thiazolyl, X is sulfur, sulfoxy or sulfone, n has a value of 4 to 7, with methyl-β-aminocrotonate and a mono or disubstituted benzaldehyde having the general formula IV in a suitable solvent.

The compounds of general formula VI can be prepared by reacting diketene in an inert solvent with a substituted aromatic five-membered heterocyclic mercapto ω-alkanol having the general formula V:

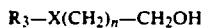

$$R_3-X(CH_2)_n-CH_2OH \quad\quad VII$$

in which $R_3$ is 4-methyl-2-thiazolyl, X is sulfur and n is between 4 to 7 inclusive.

The compounds having the general formula VII may be prepared by reacting an appropriate sodium salt of a mercapto derivative of a substituted aromatic five-membered heterocycle comprising 4-methyl-2-thiazolyl with 6-bromo-1-hexanol in an inert solvent. The resultant thioether derivative of general formula VI is consecutively oxidized utilizing m-chlorobenzoic acid to the related sulfonyl and by potassium permanganate in acetic acid to the sulfonyl analogue.

Broadly stated, the invention is a 1,4-dihydropyridine derivative of the formula I:

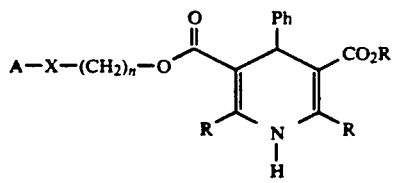

in which:
A is an azole moiety;
R is a $C_1$–$C_4$ alkyl group;
X is —$CH_2$—, —S—, —SO— or —$SO_2$—;
n is 5, 6, 7 or 8; and
Ph is a phenyl group substituted once or twice by $NO_2$, $CF_3$ or Cl groups.

Another broad aspect of the invention is a process for the preparation of the compounds of formula I or II comprising: reacting the compound of formula III in which R3 is 3-methyl-5-isoxazolyl, 3,5-dimethyl-1-pyrazolyl, or 4-methyl-2-thiazolyl, and n has a value of between 5 to 8 with methyl-β-aminocrotonate and a mono- or disubstituted benzaldehyde of the formula IV in which $R_1$ is a hydrogen, nitro, trifluoromethyl, or chloro. $R_2$ is a hydrogen or a nitro group, or a trifluoromethyl group or a chloro group, or $R_1 = R_2$ and is a chloro group.

DESCRIPTION OF THE PREFERRED EMBODIMENT

The compounds of this invention of formulae I and II are prepared, applying modified Hantzsch pyridine synthesis, by reacting the appropriately substituted aromatic five-membered heterocyclic alkyl acetoacetate or substituted aromatic five-membered heterocyclic mercapto, alkyl acetoacetate with a mono or disubstituted benzaldehyde derivative and methyl-β-aminocrotonate in isopropanol. The compounds of formula III and VI are respectively prepared by reacting diketene with an appropriately substituted aromatic five-membered heterocyclic ω-alkanol or substituted aromatic five-membered heterocyclic mercapto ω-alkanol in benzene. The related sulfoxy and sulfonyl derivative of formula VI are prepared by oxidizing the relative mercapto derivative with m-chloro-perbenzoic acid in $CH_2Cl_2$ followed by further oxidation with potassium permanganate in acetic acid. All the products in this invention are characterized by their respective nmr, ir spectra and their elemental analysis. The relative purity has been determined by HPLC. Calcium antagonistic activity of the compounds was determined at the concentration required to produce 50% inhibition of the muscarinic receptor-mediated $Ca^{2+}$-dependent contraction of guinea pig ileal longitudinal smooth muscle assay.

The compounds of formula II, wherein $R_1$ and $R_2$ were chloro, trifluoromethyl, nitro; $R_3$ is a substituted aromatic five-membered heterocycle selected from the group consisting of 3-methyl-5-isoxazolyl; 3,5-dimethyl-1-pyrazolyl and 4-methyl-2-thiazolyl, n has a value of 5 to 8, and X is $CH_2$ were prepared as follows.

An equimolecular mixture of an appropriately substituted aromatic five-membered heterocyclic alkyl acetoacetate of the formula III, a mono or disubstituted benzaldehyde of formula IV, and methyl-β-aminocrotonate in isopropanol were refluxed for a period of 12–36 hrs. The crude products were purified by elution from a silica gel column using an appropriate eluant.

The alkyl acetoacetates could, for example, be 5-(7-acetoacetoxyhept-1-yl)-3-methylisoxazole; 1-(6-acetoacetoxyhex-1-yl)-3,5-dimethylpyrazole; 2-(7-acetoacetoxyhept-1-yl)-4-methylthiazole; 2-(6-acetoacetoxyhexylthio)-4-methylthiazole; or 2-(6-acetoacetoxyhexylsulfonyl)-4-methylthiazole. The benzaldehyde could, for example, be selected from those described supra.

The acetoacetate derivatives of formula III were prepared by refluxing an equivalent mixture of diketene and appropriately substituted aromatic five-membered heterocyclic ω-alkanol of the formula V, in benzene for a period of 8–12 h. The products were purified by vacuum distillation in yields varying from 50–80%.

The heterocyclic ω-alkanols could, for example, be 7-(3-methylisoxazol-5-yl)heptan-1-ol; 6-(3,5-dimethylpyrazol-1-yl)hexan-1-ol; 7-(4-methylthiazol-2-yl)heptan-1-ol or 6-(4-methylthiazol-2-yl)thiohexan-1-ol.

The ω-hydroxyalkyl heterocyclic systems of the formula V were prepared through the lithiation of the appropriately substituted aromatic five-membered heterocycle followed by reaction with 6-bromo-hexanol, in THF at −70° C. The crude products were purified by elution from a silica gel column using different ratio of $CH_2Cl_2$-hexane. The yield varied from 50-70%.

The compounds of formula II wherein $R_1$ and $R_2$ are chloro, trifluoromethyl, nitro; $R_3$ is a substituted aromatic five-membered heterocycle selected from the group consisting of 3-methyl-5-isoxazolyl; 3,5-dimethyl-1-pyrazolyl and 4-methyl-2-thiazolyl, n has a value of 5 to 8, and X is sulfur, sulfoxy or sulfone, and n has a value of 4 to 7 have been prepared by the following method.

An equimolecular mixture of an appropriately substituted aromatic heterocyclic mercapto, sulfoxy, or sulfonyl alkyl acetoacetate of formula VI, mono or disubstituted benzaldehyde of formula IV, and methyl β-aminocrotonate in isopropanol was refluxed for a period of 12-36 hrs. The crude products were purified by silica gel column chromatography in yields varying from 70-80%.

The acetoacetates of formula VI could, for example, be 5-(7-acetoacetoxyhept-1-yl)-3-methylisoxazole; 1-(6-acetoacetoxyhex1-yl) -3,5-dimethylpyrazole; 2-(7-acetoacetoxyhept-1-yl)-4-methylthiazole; 2- (6-acetoacetoxyhexylthio)-4-methylthiazole; or 2-(6-acetoacetoxyhexylsulfonyl)-4-methylthiazole. The benzaldehydes could be selected from those described supra.

The substituted aromatic heterocyclic mercapto, sulfoxy or sulfonyl alkyl acetoacetates of formula VI were prepared by refluxing an equimolecular mixture of substituted aromatic heterocyclic mercapto alkanol of formula VII with diketene in benzene for a period of 12 h. The crude product was purified by elution from a silica gel column using $CHCl_3$ as an eluant, in almost quantitative yield. The resulting product was oxidized by m-chloroperbenzoic acid (MCPBA) in $CH_2Cl_2$ at room temperature overnight, followed by purification through elution in a silica gel column using $CHCl_3$ as an eluant, to get the related sulfoxy derivative in 68% yield. The sulfoxy derivative was further oxidized to the sulfonyl derivative using potassium permanganate in acetic acid for 4 h. The product was purified by silica gel column chromatography using chloroform-hexane (80:20) in 60% yield.

The ω-alkanol of structure VII could, for example, be 7-(3-methylisoxazol-5-yl)heptan-1-ol; 6-(3,5-dimethyl-pyrazol-1-yl)hexan-1-ol; 7-(4-methylthiazol-2-yl)heptan-1-ol or 6-(4-methylthiazol-2-yl)thiohexan-1-ol.

The substituted aromatic heterocyclic mercapto ω-alkanol of structure VII was prepared by refluxing an equimolecular mixture of an appropriately substituted mercapto heterocycle with 6-bromo-hexanol and potassium carbonate in acetone for 14 h. The crude product was purified by elution from a silica gel column using ethylacetate-methanol (99:1) in quantitative yield.

The selected compounds of this invention were tested for their calcium channel blocking activity and other possible pharmacological activity under a wide-range screening program.

More particularly, 3-[7-(3-methylisoxazol-5-yl)heptyloxycarbonyl]-5-methoxycarbonyl-2,6-dimethyl-4-(3-nitrophenyl)-1,4-dihydropyridine; 3-[7-(3-methylisoxazol-5-yl)heptyloxycarbonyl]-5-methoxycarbonyl-2,6-dimethyl-4-(3-trifluoromethylphenyl)-1,4-dihydropyridine; 3-[6-(3,5-dimethylpyrazol-1-yl)hexyloxycarbonyl]-5-methoxycarbonyl-2,6-dimethyl-4-(3-nitrophenyl)-1,4-dihydropyridine; 3-[7-(4-methylthiazol-2-yl)heptyloxycarbonyl]-5-methoxycarbonyl-2,6-dimethyl-4-(3-nitrophenyl)-1,4-dihydropyridine; the 3-[7-(4-methylthiazol-2-yl)heptyloxycarbonyl]-5-methoxycarbonyl-2,6-dimethyl-4-(3-trifluoromethylphenyl)-1,4-dihydropyridine; 3-[7-(4-methylthiazol-2-yl)heptyloxycarbonyl]-5-methoxycarbonyl-2,6-dimethyl-4-(3-chlorophenyl)-1,4-dihydropyridine; 3-[7-(4-methylthiazol-2-yl)heptyloxycarbonyl]-5-methoxycarbonyl-2,6-dimethyl-4-(2,3-dichlorophenyl)-1,4-dihydropyridine; 3-[6-(4-methylthiazol-2-yl)-thiohexyloxycarbonyl]-5-methoxycarbonyl-2,6-dimethyl-4-(3-nitrophenyl)-1,4-dihydropyridine; 3-[6-(4- methylthiazol-2-yl)-sulfoxyhexyloxycarbonyl]-5-methoxycarbonyl-2,6-dimethyl-4-(3-nitrophenyl)-1,4-dihydropyridine; 3-[6-(4-methylthiazol-2-yl)-sulfonylhexyloxycarbonyl]-5-methoxycarbonyl-2,6-dimethyl-4-(3-nitrophenyl)-1,4-dihydropyridine were tested for their calcium channel blocking activity.

Almost all the compounds tested were shown to possess very strong calcium channel blocking activity on smooth muscles and to lack negative ionotropic effect on the heart. At the concentrations which normally exhibit their Ca- blocking effect in smooth muscles, some of them have been shown to increase the heart contractile force, for example, 3-[7-(4-methylthiazol-2-yl)heptyloxycarbonyl]-5-methoxycarbonyl-2,6-dimethyl-4-(3-nitrophenyl)-1,4-dihydropyridine and 3-[6-(4-methylthiazol-2-yl)sulfonylhexyloxycarbonyl]-5-methoxycarbonyl-2,6-dimethyl-4-(3-nitrophenyl)-1,4-dihydropyridine, without changing the heart rate.

More particularly, the structure 3- [7-(4-methylthiazole-2-yl)heptyloxycarbonyl]-5-methoxycarbonyl-2,6-dimethyl-4-(3-nitrophenyl)-1,4-dihydropyridine, which has a relative potency of 4.3 ($IC_{50}$ $3.25 +/- 0.33 \times 10^{-9}M$) as compared with Nifedipine* ($IC_{50}$ $1.40 +/- 0.20 \times 10^{-8}M$) as a calcium antagonist in smooth muscle, shows about 12% positive ionotropic effect on the heart. In the same manner, compound 3-[6-(4-methylthiazol-2-yl)sulfonylhexyloxycarbonyl]-5-methoxycarbonyl-2,6-dimethyl-4-(3-nitrophenyl)-1,4-dihydropyridine which has a relative potency of 2.5 as compared with Nifedipine ($IC_{50}$ 5.57 $+/- 0.00 \times 10^{-9}M$) on smooth muscle, shows about 22% positive ionotropic effect on heart muscle, in the same concentration.

*Trademark

The mode of action of 3-[7-(4-methylthiazol-2-yl)heptyloxycarbonyl]-5-methoxycarbonyl-2,6-dimethyl-4-(3-nitrophenyl)-1,4-dihydropyridine is similar to 3-ethoxycarbonyl-5-methoxycarbonyl-4-(2,3-dichlorophenyl)-2,6-dimethyl-1,4-dihydropyridine (Felodipine, H 154/82; J. Cardiovascular Pharmacology, 1987, 10 (Suppl. 1) S60–S65), a compound in third phase of clinical trials by Astra Pharmaceuticals, because of its potency, with regard to its antihypertensive property. However, Felodipine creates tachycardia whereas 3-[7-(4-methylthiazol-2-yl)heptyloxycarbonyl]-5-methoxycarbonyl-2,6-dimethyl-4-(3-nitrophenyl)-1,4-dihydropyridine increases cardia contractile force whilst having no effect on the heart.

Upon general pharmacological screening, the selected compounds of this invention show other activities. More particularly, the structure 3-[7-(3-methylisoxazol-5-yl)heptyloxycarbonyl]-5-methoxycarbonyl-2,6-dimethyl-4-(3-nitrophenyl)-1,4-dihydropyridine and the structure 3-[7-(4-methylthiazol-2-yl)heptyloxycarbonyl]-5-methoxycarbonyl-2,6-dimethyl-4-(3-chlorophenyl)-1,4-dihydropyridine have shown very strong angiotensin inhibitory, $LTD_4$ antagonistic, anti-ulcer stressic activities. The structure 3-[6-(3,5-dimethylpyrazol-1-yl)hexyloxycarbonyl]-5-methoxycarbonyl-2,6-dimethyl-4-(3-nitrophenyl)-1,4-dihydropyridine and the structure 3-[7-(4-methylthiazol-2-yl)heptyloxycarbonyl]-5-methoxycarbonyl-2,6-dimethyl-4-(3-trifluoromethylphenyl)-1,4-dihydropyridine possessed very strong anti-inflammatory activity in addition to the other activities mentioned for the structure 3-[7-(3-methylisoxazol-5-yl)heptyloxycarbonyl]-5-methoxycarbonyl-2,6-dimethyl-4-(3-nitrophenyl)-1,4-dihydropyridine.

EXAMPLE 1

3-[7-(3-Methylisoxazol-5-yl)heptyloxycarbonyl]-5-methoxycarbonyl-2,6-dimethyl-4-(3-nitrophenyl)- 1,4-dihydropyridine. (1)

$R_1$ = 3-methylisoxazol-5-yl; n=6; $R_2$=m-$NO_2$; X=$CH_2$. (See schematic representation of reaction given herebelow).

7-(3-methylisoxazol-5-yl)heptylacetoacetate (1.967 g, 0.007 l mol) was added to a solution of methyl-β-aminocrotonate (0.805 g, 0.007 mol) and m-nitrobenzaldehyde (1.057 g, 0.007 mol) in isopropanol (35 mL). The reaction mixture was heated under reflux for 12 h and then concentrated under reduced pressure. The residual oil was purified by elution from a silica gel column using dichloromethane-hexane (9:1, v/v) as eluant to give 3-[7-(3-methylisoxazol-5-yl)heptyloxycarbonyl]-5-methoxycarbonyl-2,6-dimethyl-4-(3-nitrophenyl)-1,4-dihydropyridine (60%) as a pale yellow thick oil. IR (neat) 3330 (NH) and 1701 and 1676 ($CO_2R$)cm$^{-1}$, NMR ($CDCl_3$) 1.20-1.40 (m, 6H, —($CH_2$)$_3$), 1.56-1.74 (m, 4H, —($CH_2$)$_2$), 2.30 (S, 3H, Me), 2.39 (S, 3H, Me), 2.72 (t, J =9 Hz, 2H, $CH_2$-Het), 3.70 (S, 3H, $CO_2$Me), 3.99-4.16 (m, 2H,—$OCH_2$), 5.14 (S, 1H, H-4), 5.89 (S, 1H, Het-H), 7.06 (S, 1H, NH), 7.38-8.14 (m, 4H, H-2 , H-4', H-5', H-6'). Analysis found: C, 63.48; H, 6.45; N, 7.99. Required: C, 63.39; H, 6.50; N, 8.21 ($C_{27}H_{33}N_3O_7$).

Schematic for Example 1

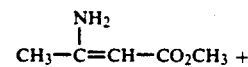

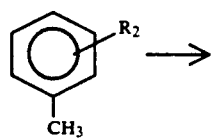

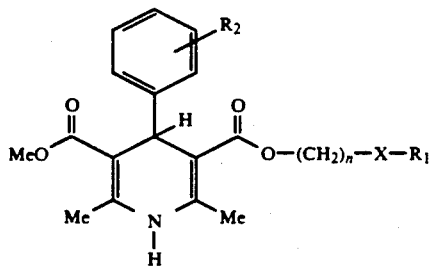

By procedures similar to those used in Example 1, and starting with the appropriately substituted aromatic five-membered heterocyclic alkylacetoacetate and benzaldehyde derivatives, the following compounds were prepared.

EXAMPLE 2

3-[7-(3-Methylisoxazol-5-yl)heptyloxycarbonyl]-5-methoxycarbonyl-2,6-dimethyl-4-(2-nitrophenyl) -1,4-dihydropyridine. (2)

$R_1$=3-methylisoxazol-5-yl; n =6; $R_2$=O-$NO_2$; X=$CH_2$.

Thick yellow oil, (20%), IR (neat) 3335 (NH), 1726 and 1696 ($CO_2R$)cm$^{-1}$; NMR ($CDCl_3$) 1.08-1.40 (m, 6H, ($CH_2$)$_3$), 1.50-1.72 (m, 4H, ($CH_2$)2), 2.28 (S, 3H, Me), 2.30 (S, 3H, Me), 2.36 (S, 3H, Me), 2.96 (t, J=9 Hz, 2H, —$CH_2$-Het), 3.60 (S, 3H, $CO_2$Me), 3.98-4.10 (m, 2H, —$CH_2$—O)<, 5.80 (S, 1H, H-4), 5.85 (S, 1H, H-Het), 6.55 (S, 1H, NH), 7.22-7.74 (m, 4H, H-3', H-4', H-5', H-6'). Analysis found: C, 63.25; H, 6.52; N, 8.33. Required: C, 63.39; H, 6.50; N, 8.21 ($C_{27}H_{33}N_3O_7$).

EXAMPLE 3

3-[7-(3-Methylisoxazol-5-yl)heptyloxycarbonyl]-5-methoxycarbonyl-2,6-dimethyl-4-(3-trifluoromethylphenyl)-1,4-dihydropyridine. (3)

$R_1$ = 3-methylisoxazol-5-yl; n=6; $R_2$=m-$CF_3$; X=$CH_2$.

Thick oil, (30%); IR (neat) 3330 (NH) 1697 and 1660 ($CO_2R$)cm$^{-1}$. NMR ($CDCl_3$) 1.20-1.40 (m, 6H, ($CH_2$)$_3$), 1.54-1.74 (m, 4H, ($CH_2$)$_2$), 2.30 (S, 3H, Me), 2.36 (S, 3H, Me), 2.38 (S, 3H, Me), 2.72 (t, J=9 Hz, 2H, $CH_2$-Het), 3.69 (S, 3H, $CO_2$Me), 3.99-4.20 (m, 2H, —$OCH_2$), 5.09 (S, 1H, H-4), 5.86 (S, 1H, H-Het), 6.36 (S, 1H, NH), 7.32-7.60 (m, 4H, H-2', H-4', H-5', H-6'). Analysis found: C, 63.05; H, 6.20; N, 5.18. Required: C, 62.91; H, 6.22; N, 5.24 ($C_{28}H_{33}F_3N_2O_5$).

EXAMPLE 4

3-[7-(3-Methylisoxazol-5-yl)heptyloxycarbonyl]-5-methoxycarbonyl-2,6-dimethyl-4-(2-trifluoromethylphenyl)-1,4-dihydropyridine. (4)

$R_1$ = 3-methylisoxazol-5-yl; n=6; $R_2$=O-$CH_3$; X =$CH_2$.

Thick yellow oil, (22%); IR (neat) 3335 (NH), 1698 and 1686 ($CO_2R$)cm$^{-1}$; NMR ($CDCl_3$) 1.14-1.36 (m, 6H, ($CH_2$)$_3$), 1.50-1.70 (m, 4H, ($CH_2$)$_2$), 2.28 (S, 6H, Me-2, Me-6), 2.32 (S, 3H, Me-Het), 2.69 (t, J=9 Hz, $CH_2$-Het), 3.61 (S, 3H, $CO_2$Me), 3.92-4.12 (m, 2H, 0—$CH_2$), 5.57 (S, 1H, H-4), 5.85 (S, 1H, H-Het), 6.55 (S, 1H, NH), 7.20-7.59 (m, 4H, H-3', H-4', H-5', H-6'). Analysis found: C, 63.05; H, 6.31; N, 5.08. Required: C, 62.91; H, 6.22; N, 5.24 ($C_{28}H_{33}F_3N_2O_5$).

EXAMPLE 5

3-[6-(3,5-Dimethylpyrazol-1-yl)hexyloxycarbonyl]-5-methoxycarbonyl-2,6-dimethyl-4-(3-nitrophenyl) -1,4-dihydropyridine.

$R_1$ = 3,5-dimethylpyrazol-1-yl; n=5; $R_2$=m-$NO_2$; X=$CH_2$.

Thick yellow oil, (45%); IR (neat) 3335 (NH), 1700 and 1688 ($CO_2R$)cm$^{-1}$; NMR ($CDCl_3$) 1.23-1.35 (m, 4H, ($CH_2$)$_2$), 1.60 (q, J=6 Hz, 2H, $CH_2$), 1.75 (t, J=6 Hz, 2H, $CH_2$), 2.24 (S, 6H, Me-2, Me-6), 2.36 (S, 6H, 2Me-Het), 3.67 (S, 3H, $CO_2$Me), 3.90-4.10 (m, 4H, O—$CH_2$ and $CH_2$—Het), 5.11 (S, 1H, H-4), 5.90 (S, 1H, H-Het), 6.75 (S, 1H, NH), 7.34-8.16 (m, 4H, H-2', H-4', H-5', H-6'). Analysis found: C, 63.38; H. 6.68; N, 11.13. Required: C, 63.52; H, 6.71; N, 10.97 ($C_{27}H_{34}N_4O_6$).

EXAMPLE 6

3-[6-(3,5-Dimethylpyrazol-1-yl)hexyloxycarbonyl]-5-methoxycarbonyl-2,6-dimethyl-4-(2-nitrophenyl)-1,4-dihydropyridine. (6)

$R_1$ = 3,5-dimethylpyrazol-1-yl; n = 5; $R_2$ = O-$NO_2$; X = $CH_2$.

Thick yellow oil, (35%); IR (neat) 3340 (NH), 1694 and 1654 ($CO_2R$)cm$^{-1}$; NMR ($CDCl_3$) 1.08–1.30 (m, 4H, ($CH_2$)$_2$), 1.54 (q, JL = 6 Hz, 2H, $CH_2$), 1.71 (q, J = 6 Hz, 2H, CH2), 2.23 (S, 6H, Me-3, Me-6), 2.31 (S, 3H, Me-Het), 2.36 (S, 3H, Me-Het), 3.60 (S, 3H, $CO_2Me$), 3.89–4.10 (m, 4H, —$OCH_2$ and $CH_2$—Het), 5.79 (S, 2H, H-4 and H-Het), 6.06 (S, 1H, NH), 7.22–7.74 (m, 4H, H-3', H-4', H-5', H-6'). Analysis found: C, 63.71; H, 6.79; N, 10.81. Required: C, 63.52; H, 6.71; N, 10.97 ($C_{27}H_{34}N_4O_6$).

EXAMPLE 7

3-[6-(3,5-Dimethylpyrazol-1-yl)hexyloxycarbonyl]-5-methoxycarbonyl-2,6-dimethyl-4-(3-trifluorophenyl)-1,4-dihydropyridine. (7)

$R_1$ = 3,5-dimethylpyrazol-1-yl; n = 5; $R_2$ = m-$CF_3$; X = $CH_2$.

Thick yellow oil, (40%); IR (neat) 3335 (NH), 1697 and 1687 ($CO_2R$)cm$^{-1}$; NMR ($CDCl_3$) 1.20–1.32 (m, 4H, ($CH_2$)$_2$), 1.56 (q, J = 6 Hz, 2H, $CH_2$), 1.74 (q, J = 6 Hz, 2H, $CH_2$), 2.26 (S, 6H, Me-2, Me-6), 2.34 (S, 6H, 2Me-Het), 3.66. (S, 3H, $CO_2Me$), 3.90–4.12 (m, 4H, O—$CH_2$ and $CH_2$—Het), 5.06 (S, 1H, H-4), 5.80 (S, 1H, H-Het), 6.62 (S, 1H, NH), 7.28–7.56 (m, 4H, H-2', H-4', H-5', H-6'). Analysis found: C, 63.15; H, 6.51; N, 7.75. Required: C, 63 03; H, 6.42; N, 7.88 ($C_{28}H_{34}F_3N_3O_4$).

EXAMPLE 8

3-[6-(3,5-Dimethylpyrazol-1-yl)hexyloxycarbonyl]-5-methoxycarbonyl-2,6-dimethyl-4-(2-trifluorophenyl)-1,4-dihydropyridine. (8)

$T_1$ = 3,5-dimethylpyrazol-1-yl; n = 5; $R_2$ = 0-$CF_3$; X = $CH_2$.

Thick yellow oil, (25%); IR (neat) 3340 (NH), 1700 and 1698 ($CO_2R$)cm$^{-1}$; NMR ($CDCl_3$) 1.10–1.30 (m, 4H, ($CH_2$)$_2$), 1.75 (q, J = 6 Hz, 2H, —$CH_2$). 2.25 (S, 6H, Me-2, Me-6), 2.30 (S, 6H, 2Me-Het), 3.60 (S, 3H, $CO_2Me$), 3.90–4.10 (m, 4H, O—$CH_2$, $CH_2$—Het), 5.56 (S, 1H, H-4), 5.80 (S, 1H, H-Het), 6.28 (S, 1H, NH), 7.20–7.60 (m, 4H, H-3', H-4', H-5', H-6'). Analysis found: C, 62.91; H, 6.38; N, 8.03. Required: C, 63.03; H, 6.42; N, 7.88 ($C_{28}H_{34}F_3N_3O_4$).

EXAMPLE 9

3-[6-(3,5-Dimethylpyrazol-1-yl)hexyloxycarbonyl]-5-methoxycarbonyl-2,6-dimethyl-4-(3-chlorophenyl)-1,4-dihydropyridine. (9)

$R_1$ = 3,5-dimethylpyrazol-1-yl; n = 5; $R_2$ = m-Cl; X = $CH_2$.

Thick yellow oil, (50%); IR (neat) 3330 (NH), 1701 and 1655 ($CO_2R$)cm$^{-1}$; NMR ($CDCl_3$) 1.24–1.36 (m, 4H, -($CH_2$)$_2$), 1.61 (q, J-6 Hz, 2H, $CH_2$), 1.76 (q, J = 6 Hz, 2H, —$CH_2$), 2.24 (S, 6H, Me-2, Me-6), 2.34 (S, 6H, 2Me-Het), 3.67 (S, 3H, $CO_2Me$), 3.91–4.19 (m, 4H, $CH_2$—0 and $CH_2$—Het), 5.01 (S, 1H, H-4), 5.30 (S, 1H, H-Het), 5.81 (S, 1H, NH), 7.08–7.30 (m, 4H, H-2', H'-4', H-5', H-6'). Analysis found: C, 65.12; H, 6.69; N, 8.34; Cl, 7.18. Required: C, 64.99; H, 6.67; N, 8.42; Cl, 7.10 ($C_{26}H_{33}ClN_3O_4$).

EXAMPLE 10

3-[6-(3,5-Dimethylpyrazol-1-yl)hexyloxycarbonyl]-5-methoxycarbonyl-2,6-dimethyl-4-(2-chlorophenyl)-1,4-dihydropyridine. (10)

$R_1$ = 3,5-dimethylpyrazol-1-yl; n = 5; $R_2$ = 0-Cl; X = $CH_2$.

Thick yellow oil, (25%); IR (neat) 3335 (NH), 1699 and 1657 ($CO_2R$)cm$^{-1}$; NMR ($CDCl_3$) 1.15–1.35 (m, 4H, ($CH_2$)$_2$), 1.60 (q, J = 6 Hz, 2H, $CH_2$), 1.75 (q, J-6 Hz, 2H, —$CH_2$), 2.26 (S, 6H, Me-2, Me-6), 2.30 (S, 6H, 2Me-Het), 3.65 (S, 3H, $CO_2Me$), 3.90–4.10 (m, 4H, $CH_2$—0 and $CH_2$—Het), 5.40 (S, 1H, H-4), 5.80 (S, 1H, H-Het), 6.22 (S, 1H, NH), 7.00–7.42 (m, 4H, H-3', H-4', H-5', H-6'). Analysis found: C, 64.85; H, 6.62; N, 8.53; Cl, 7.03. Required: C, 64.99; H, 6.67; N, 8.42; Cl, 7.10 ($C_{27}H_{33}ClN_3O_4$).

EXAMPLE 11

3-[7-(4-Methylthiazol-2-yl)heptyloxycarbonyl]-5-methoxycarbonyl-2,6-dimethyl-4-(3-nitrophenyl)-1,4-dihydropyridine. (11)

$R_1$ = 4-methylthiazol-2-yl; n = 6; $R_2$ = m-$NO_2$; X = $CH_2$.

Thick yellow oil, (50%); IR (neat) 3330 (NH), 1696 and 1691 ($CO_2R$)cm$^{-1}$; NMR ($CDCl_3$) 1.20–1.40 (m, 6H, ($CH_2$)$_3$), 1.60 (q, J = 6 Hz, 2H, $CH_2$), 1.75 (q, J = 6 Hz, 2H, —$CH_2$), 2.35 (S, 6H, Me-2, Me-6), 2.42 (S, 3H, Me-Het), 2.98 (t, J-9 Hz, 2H, $CH_2$—Het), 3.66 (S, 3H, $CO_2Me$), 3.96–4.12 (m, 2H, $CH_2$—O), 5.10 (S, 1H, H-4), 6.54 (S, 1H, H-Het), 6.76 (S, 1H, NH), 7.35–8.15 (m, 4H, H-2', H-4', H-5', H-6'). Analysis found: C, 61.35; H, 6.25; N, 8.10; S, 6.00. Required: C, 61.46; H, 6.31; N, 7.96; S, 6.08 ($C_{27}H_{33}N_3O_6S$).

EXAMPLE 12

3-[7-(4-Methylthiazol-2-yl)heptyloxycarbonyl]-5-methoxycarbonyl-2,6-dimethyl-4-(2-nitrophenyl)-1,4-dihydropyridine. (12)

$R_1$ = 4-methylthiazol-2-yl; n = 6; $R_2$ = O-$NO_2$; X = $CH_2$.

Thick yellow oil, (25%); IR (neat) 3335 (NH), 1698 and 1687 ($CO_2R$)cm$^{-1}$; NMR ($CDCl_3$) 1.20–1.40 (m, 6H, ($CH_2$)$_3$), 1.55 (q, J = 6 Hz, 2H, $CH_2$), 1.75 (q, J = 6 Hz, 2H, $CH_2$), 2.30 (S, 3H, Me-6), 2.35 (S, 3H, Me-2), 2.40 (S, 3H, Me-Het), 2.95 (t, J = 9 Hz, 2H, $CH_2$—Het), 3.60 (S, 3H, $CO_2Me$), 3.95–4.10 (m, 2H, $CH_2$—O), 5.80 (S, 1H, H-4), 6.40 (S, 1H, H-Het), 6.74 (S, 1H, NH), 7.20–7.75 (m, 4H, H-3', H-4', H-5', H-6'). Analysis found: C, 61.53; H, 6.40; N, 7.78; S, 6.21. Required: C, 61.46; H, 6.31; N, 7.96; S, 6.08 ($C_{27}H_{33}N_3O_6S$).

EXAMPLE 13

3-[7-(4-Methylthiazol-2-yl)heptyloxycarbonyl]-5-methoxycarbonyl-2,6-dimethyl-4-(3-trifluoromethylphenyl)-1,4-dihydropyridine. (13)

$R_1$ = 4-methylthiazol-2-yl; n = 6; $R_2$ = m-$CF_3$; X = $CH_2$.

Thick yellow oil, (40%); IR (neat) 3335 (NH), 1699 and 1660 ($CO_2R$)cm$^{-1}$; NMR ($CDCl_3$) 1.20–1.40 (m, 6H, ($CH_2$)$_3$), 1.55 (q, J = 6 Hz, 2H, $CH_2$), 1.76 (q, J = 6 Hz, 2H, $CH_2$), 2.30 (S, 6H, Me-2, Me-6), 2.42 (S, 3H, Me-Het), 2.98 (t, J = 9 Hz, 2H, $CH_2$—Het), 3.66 (S, 3H, $CO_2Me$), 3.94–4.14 (m, 2H, $CH_2$—O), 5.07 (S, 1H, H-4), 6.74 (S, 1H, H-Het), 6.78 (S, 1H, NH), 7.30–7.56 (m, 4H, H-2', H-4', H-5', H-6'). Analysis found: C, 60.91; H, 5.96; N, 5.14; S, 5.93. Required: C, 61.08; H, 6.04; N, 5.09; S, 5.82 ($C_{28}H_{33}F_3N_3O_4S$).

EXAMPLE 14

3-[7-(4-Methylthiazol-2-yl)heptyloxycarbonyl]-5-methoxycarbonyl-2,6-dimethyl-4-(2-trifluoromethylphenyl)-1,4-dihydropyridine. (14)

$R_1$ = 4-methylthiazol-2-yl; n = 6; $R_2$ = O-$CF_3$; X = $CH_2$.

Thick yellow oil, (15%); IR (neat) 3340 (NH), 1700 and 690 ($CO_2R$)$cm^{-1}$; NMR ($CDCl_3$) 1.12–1.42 (m, 6H, ($CH_2$)$_3$), 1.55 (q, J=6 Hz, 2H, $CH_2$), 1.75 (q, J=6 Hz, 2H, $CH_2$), 2.22 (S, 6H, Me-2, Me-6), 2.44 (S, 3H, Me-Het), 2.96 (S, J=9 Hz, 2H, $CH_2$—Het), 3.62 (S, 3H, $CO_2Me$), 3.92–4.12 (m, 2H, $CH_2$—O), 5.58 (S, 1H, H-4), 6.06 (S, 1H, H-Het), 6.75 (S, 1H, NH), 7.20–7.60 (m, 4H, H-3′, H-4′, H-5′, H-6′). Analysis found: C, 61.15; H, 6.11; N, 4.96; S, 5.70. Required: C, 61.08; H, 6.04; N, 5.09; S, 5.82 ($C_{28}H_{33}F_3N_2O_4S$).

EXAMPLE 15

3-[7-(4-Methylthiazol-2-yl)heptyloxycarbonyl]-5-methoxycarbonyl-2,6-dimethyl-4-(3-chlorophenyl)-1,4-dihydropyridine. (15)

$R_1$ = 4-methylthiazol-2-yl; n = 6; $R_2$ = m-Cl; X = $CH_2$.

Thick yellow oil, (50%); IR (neat) 3335 (NH), 1698 and 1682 ($CO_2R$)$cm^{-1}$; NMR ($CDCl_3$) 1.20–1.44 (m, 6H, ($CH_2$)$_3$), 1.60 (q, J=6 Hz, 2H, $CH_2$), 1.88 (q, J=6 Hz, 2H, $CH_2$), 2.34 (S, 6H, Me-2, Me-6), 2.44 (S, 3H, Me-Het), 2.99 (t, J=9 Hz, 2H, $CH_2$—Het), 3.68 (S, 3H, $CO_2Me$), 3.96–4.18 (m, 2H, $CH_2$—O), 5.01 (S, 1H, H-4), 6.76 (S, 2H, H-Het, NH), 7.08–7.28 (m, 4H, H-3′, H-4′, H-5′, H-6′). Analysis found: C, 62.58; H, 6.39; N, 5.50; Cl, 6.92; S, 6.13. Required: C, 62.72; H, 6.42; N, 5.42; Cl, 6.86; S, 6.20 ($C_{27}H_{33}ClN_2O_4S$).

EXAMPLE 16

3-[7-(4-Methylthiazol-2-yl)heptyloxycarbonyl]-5-methoxycarbonyl-2,6-dimethyl-4-(2-chlorophenyl)-1,4-dihydropyridine. (16)

$R_1$ = 4-methylthiazol-2-yl; n = 6; $R_2$ = O-Cl; X = $CH_2$.

Thick yellow oil, (20%); IR (neat) 3335 (NH), 1696 and 1658 ($CO_2R$)$cm^{-1}$; NMR ($CDCl_3$) 1.12–1.40 (m, 6H, ($CH_2$)$_3$), 1.59 (q, J=6 Hz, 2H, $CH_2$), 1.76 (q, J=6 Hz, 2H, CH2), 2.30 (S, 3H, Me-6), 2.32 (S, 3H, Me-2), 2.44 (S, 3H, Me-Het), 2.98 (t, J=9 Hz, 2H, $CH_2$—Het), 3.65 (S, 3H, $CO_2Me$), 3.99–4.12 (m, 2H, $CH_2$—O), 5.41 (S, 1H, H-4), 6.12 (S, 1H, H-Het), 6.75 (S, 1H, NH), 7.00–7.42 (m, 4H, H-2′, H-4′, H-5′, H-6′). Analysis found: C, 62.88; H, 6.50; N, 5.40; Cl, 8.76; S, 6.05. Required: C, 62.72; H, 6.42; N, 5.42; Cl, 6.86; S, 6.20 ($C_{27}H_{33}ClN_2O_4S$).

EXAMPLE 17

3-[7-(4-Methylthiazol-2-yl)heptyloxycarbonyl]-5-methoxycarbonyl-2,6-dimethyl-4-(2,3-dichlorophenyl)-1,4-dihydropyridine. (17)

$R_1$ = 4-methylthiazol-2-yl; n = 6; $R_2$ = 2,3-dichloro; X = $CH_2$. Colorless prisms, mp 130°–131° C., (25%); IR (KBr) 3340 (NH), 1699 and 1685 ($CO_2R$)$cm^{-1}$; NMR ($CDCl_3$) 1.10–1.85 (m, 10H, ($CH_2$)$_5$), 2.25 (S, 3H, Me-6), 2.30 (S, 3H, Me-2), 2.42 (S, 3H, Me-Het), 2.96 (t, J=9 Hz, 2H, $CH_2$—Het), 3.61 (S, 3H, $CO_2Me$), 3.92–4.15 (m, 2H, $CH_2$—O), 5.45 (S, 1H, H-4), 6.50 (S, 1H, H-Het), 6.71 (S, 1H NH) 7.00–7.33 (m, 3H H-4′, H-5′, H-6′). Analysis found: C, 58.92; H, 5.88; N, 4.95; Cl, 13.05; S, 5.74. Required: C, 58.80; H, 5.85; N, 5.08; Cl, 12.86; S, 5.81 ($C_{27}H_{32}Cl_2N_2O_4S$).

EXAMPLE 18

3-[6-(4-Methylthiazol-2-yl)thiohexyloxycarbonyl]-5-methoxycarbonyl-2,6-dimethyl-4-(3-nitrophenyl)-1,4-dihydropyridine. (18)

$R_1$ = 4-methylthiazol-2-yl; n = 6; $R_2$ = m-$NO_2$; X = S.

Yellow oil (80%); IR (neat) 3320 (NH), 1700 and 1685 ($CO_2R$)$cm^{-1}$; NMR ($CDCl_3$) 1.20–1.80 (m, 8H, ($CH_2$)$_4$), 2.36 (S, 6H, Me-2, Me-6), 2.42 (S, 3H, Me-Het), 3.16 (t, J=9 Hz, 2H, $CH_2$—S), 3.66 (S, 3H, $CO_2Me$), 4.00–4.18 (m, 2H, $CH_2$—O), 5.14 (S, 1H, H-4), 6.68 (S, 1H, H-Het), 6.80 (S, 1H, NH), 7.36–8.16 (m, 3H, H-2′, H-4′, H-5′, H-6′). Analysis found: C, 57.38; H, 5.80; N, 7.65; S, 11.68. Required: C, 57.23; H, 5.73; N, 7.70; S, 11.75 ($C_{26}H_{31}N_3O_6S_2$).

EXAMPLE 19

3-[6-(4-Methylthiazol-2-yl)sulfonylhexyloxycarbonyl]-5-methoxycarbonyl-2,6-dimethyl-4-(3-nitrophenyl)-1,4-dihydropyridine. (19)

$R_1$ = 4-methylthiazol-2-yl; n = 6; $R_2$ = m-$NO_2$; X = $SO_2$.

Colorless prisms, mp 102°–105° C. (75%); IR (KBr) 3375 (NH), 1698 and 1669 ($CO_2$)$cm^{-1}$; NMR ($CDCl_3$) 1.18–1.84 (m, 8H, ($CH_2$)$_4$), 2.32 (S, 6H, Me-2, Me-6), 2.52 (S, 3H, Me-Het), 3.35 (t, J=9 Hz, 2H, $CH_2$—$SO_2$), 3.65 (S, 3H, $CO_2Me$), 3.90–4.10 (m, 2H, $CH_2$—O), 5.10 (S, 1H, H-4), 6.48 (S, 1H, H-Het), 7.34–8.10 (m, 5H, NH, H-2′, H-4′, H-5′, H-6′). Analysis found: C, 54.20; H, 5.50; N, 7.15; S, 11.00. Required: C, 54.06; H, 5.41; N, 7.27; S, 11.10 ($C_{26}H_{31}N_3O_8S_2$).

EXAMPLE 20

3-[6-(4-Methylthiazol-2-yl)sulfinylhexyloxycarbonyl]-5-methoxycarbonyl-2,6-dimethyl-4-(3-nitrophenyl)-1,4-dihydropyridine. (20)

$R_1$ = 4-methylthiazol-2-yl; n = 6; $R_2$ = 3-$NO_2$; X = SO. (See schematic representation of reaction given herebelow)

A solution of m-chloroperbenzoic acid (0.156g, 0.001 mol) in dichloromethane (5mL) was added to a solution of 3-[6-(4-methylthiazol-2-yl) thiohexyloxy-carbonyl]-5-methoxycarbonyl-2,6-dimethyl-4-(3-nitrophenyl)-1,4-dihydropyridine (18) (0.545 g, 0.001 mol) in dichloromethane (10 mL) at room temperature with agitation. Stirring under the same conditions was maintained for 2 h. The excess peracid was decomposed by 10% solution of sodium sulfite. The organic layer was separated and washed with 5% sodium bicarbonate solution in order to extract m-chlorobenzoic acid, followed by washing with water and drying over anhydrous sodium sulfate. The solvent was removed under reduced pressure, and the residual oil was purified by elution from a silica gel column using chloroform-hexane (8:2, v/v) as eluant to give 3-[6-(4-methylthiazol-2-yl)sulfinylhexyloxycarbonyl]-5-methoxycarbonyl-2,6-dimethyl-4-(3- nitrophenyl)-1,4-dihydropyridine (65%) as colorless prisms, mp 81°–83° C. IR (KBr) 3365 (NH) 1695 and 1652 ($CO_2R$) 1033 (SO)cm-1, NMR ($CDCl_3$) 1.22–1.74 (m, 8H, ($CH_2$)$_4$), 2.36 (S, 6H, Me-2, Me-6) 2.52 (S, 3H, Me-HEt),3.02–3.22 (m, 2H, $CH_2$—SO), 3.68 (S, 3H, $CO_2Me$), 3.96–4.14 (m, 2H, $CH_2$—O), 5.12 (S, 1H, H-4), 6.56 (S, 1H, H-HEt), 7.26 (S, 1H, NH), 7.38–8.14 (m, 4H, H-2′, H-4′, H-5′, H-6′). Analysis found: C, 55.75; H, 5.64; N, 7.35; S, 11.30. Required: C, 55.66; H, 5.56; N, 7.48; S, 11.42 ($C_{26}H_{31}N_3O_7S_2$).

Schematic representation of reaction

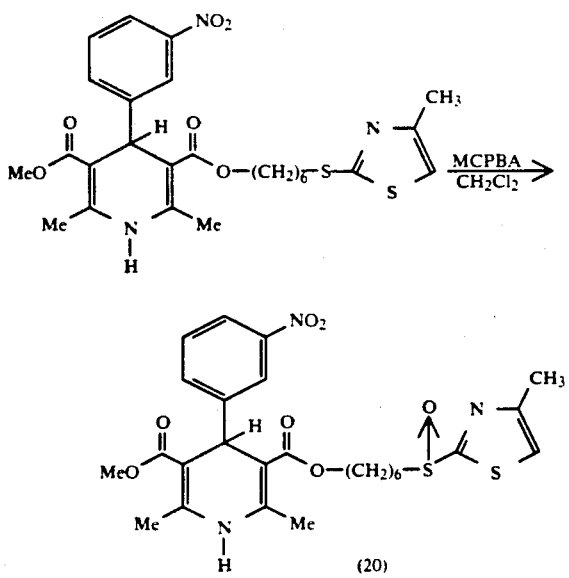

EXAMPLE 21

5-(7-Acetoacetoxyhept-1-yl)-3-methylisoxazole. (21) (See schematic representation of the reaction given herebelow)

To a mixture of 7-(3-methylisoxazol-5-yl)heptan-1-ol (1.97 g, 0.01 mol) and anhydrous sodium acetate (0.080 g) in benzene (20mL) was added a solution of diketene (1.84 g, 0.022 mol) in benzene (6 mL) dropwise. The mixture was refluxed for 12 h. After the removal of benzene under reduced pressure, the crude product was purified by elution from a silica gel column using dichloromethane-hexane (9:1 v/v) as eluant to give 5-(7-acetoacetoxyhept-1-yl)-3-methylisoxazole (21) (70%) as a yellow oil. IR (neat) 1740 ($CO_2$), 1718 (CO)cm$^{-1}$; NMR (CDCl$_3$) 1.12–1.95 (m, 10H, ($CH_2$)$_5$), 2.35 (S, 6H, Me-Het, CO-Me), 2.70 (t, J=9 Hz, 2H, $CH_2$—Het), 3.49 (S, 2H, CO—$CH_2$—COMe), 4.14 (t, J=6 Hz, 2H, O—$CH_2$), 5.80 (S, 1H, H-Het). Analysis found: C, 64.11; H, 8.31; N, 4.72. Required: C, 64.02; H, 8.24; N, 5.00 ($C_{15}H_{23}NO_4$).

Schematic of Example 21

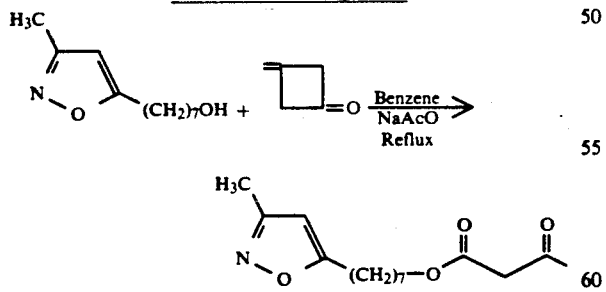

Following the same procedure as Example 21, and starting with the appropriately substituted ω-heterocyclic alkanol, the following compounds were prepared.

EXAMPLE 22

1-(6-Acetoacetoxyhex-1-yl)-3,5-dimethylpyrazole. (22)

Yellow oil (75%). IR (neat) 1741($CO_2$) 1718(CO)cm$^{-1}$; NMR (CDCl$_3$) 1.20–2.10 (m, 8H, ($CH_2$)$_4$), 2.30 (S, 9H, Me-3, Me-5, —COMe), 3.50 (S, 2H, CO—$CH_2$—CO), 3.88–4.32 (m, 4H, $CH_2$N,—$CH_2$O), 5.81 (S, 1H, H-Het). Analysis found: C, 64.29; H, 8.71; N, 9.85. Required: C, 64.23; H, 8.62; N, 10.04 ($C_{15}H_{24}N_2O_3$).

EXAMPLE 23

2-(7-Acetoacetoxyhept-1-yl)-4-methylthiazole. (23)

Yellow oil (80%). IR (neat) 1740($CO_2$), 1716(CO)cm$^{-1}$; NMR (CDCl$_3$) 1.30–1.50 (m, 6H, ($CH_2$)$_3$), 1.65 (q, J=6 Hz, 2H, $CH_2$), 1.78 (q, J=6 Hz, 2H, —$CH_2$), 2.28 (S, 3H, Me-Het), 2.40 (S, 3H, $CH_3$CO), 2.96 (t, J=9 Hz, 2H, —$CH_2$—Het), 3.46 (S, 2H, CO—$CH_2$—CO), 4.15 9t, J=9 Hz, 2H, —$CH_2$O), 6.72 (S, 1H, H-Het). Analysis found: C, 60.68; H, 7.83; N, 4.21; S, 10.55. Required: C, 60.56; H, 7.79; N, 4.73; S, 10.78 ($C_{15}H_{23}NO_3S$).

EXAMPLE 24

2-(6-Acetoacetoxyhexylthio)-4-methylthiazole. (24)

Yellow oil (99%). IR (neat) 1742($CO_2$), 1715(CO)cm$^{-1}$; NMR (CDCl$_3$) 1.25–2.10 (m, 8H, ($CH_2$)$_4$), 2.23 (S, 3H, Me-Het), 2.36 (S, 3H, CO—$CH_3$), 3.16 (t, J=9 Hz, 2H, —$CH_2$—S), 3.46 (S, 2H, CO—$CH_2$—CO), 4.14 (t, J=9 Hz, 2H, —$CH_2$—O), 6.77 (S, 1H, H-Het). Analysis found: C, 53.35; H, 6.79; N, 4.23; S, 20.23. Required: C, 53.30; H, 6.71; N, 4.46; S, 2032 ($C_{14}H_{21}NO_3S_2$).

EXAMPLE 25

2-(6-Acetoacetoxyhexylsulfonyl)-4-methylthiazole. (25) (See the schematic representation of reaction given herebelow)

2-(6-Acetoacetoxyhexylthio)-4-methylthiazole (3.15 g, 0.01 mol) was dissolved in a mixture of glacial acetic acid (125 mL) and water (25 mL) at room temperature. To the mixture was added fractionwise (3.32 g, 0.021 mol) of KMnO$_4$ while stirring, keeping the temperature at approximately 25° C. for 2h. The mixture was stirred at room temperature for an additional 1½ h, then decolorized with H$_2$O$_2$ (30%). Ice water (200 mL) was added to the mixture and filtered. The filtrate was extracted with diethyl ether. After the removal of the solvent, under reduced pressure, the crude product was purified by elution from a silica gel column using chloroform-hexane (8:2 v/v) as eluant to give 2-(6-acetoacetoxyhexylsulfonyl)-4-methylthiazole (25) (25%) as a yellow oil. IR (neat) 1741 ($CO_2$), 1719(—CO)cm$^{-1}$; NMR (CDCl$_3$) 1.18–2.00 (m, 8H, ($CH_2$)$_4$), 2.26 (S, 3H, Me-Het), 2.55 (S, 3H, $CO_2$Me), 3.20–3.56 (m, 4H, —$CH_2$—$SO_2$ and CO—$CH_2$—CO), 3.96–4.23 (t, J=9 Hz, 3H, —$CH_2$—:O), 7.34 (S, 1H, H-Het). Analysis found: C, 48 46; H, 6.17; N, 3.87; S, 18.37. Required: C, 48.39; H, 6.09; N, 4.05; S, 18.45 ($C_{14}H_{21}NO_5S_2$).

Schematic for Example 25

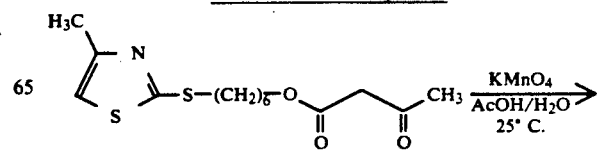

-continued
Schematic for Example 25

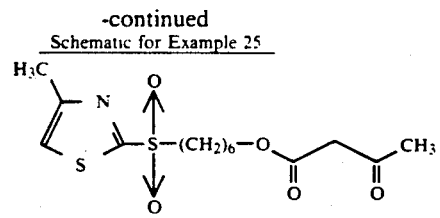

EXAMPLE 26

7-(3-Methylisoxazol-5-yl)heptan-1-ol. (26) (See the schematic representation of reaction given herebelow)

To a solution of diisopropylamine (9.8 mL, 0.07 mol) in tetrahydrofuran (17.5mL) at −5° C. and under nitrogen, was added n-butyllithium (1.6M) in hexane (23.1 mL, 0.78 mol) dropwise keeping the temperature constant. After the addition was complete, the solution was cooled to −60° C. and 3,5-dimethylisoxazole (2.91 g, 0.03 mol) in THF (7.5 mL) was added dropwise. The mixture was stirred for an additional 1 h at −60° C., then added via a nitrogen purge to 6-bromo-1-hexanol (3.62 g, 0.02 mol) in THF (10 mL), and chilled to −60° C. while stirring. The mixture was allowed to gradually warm to room temperature and then stirred overnight.

After quenching with saturated $NH_4Cl$ solution (7 mL), the mixture was extracted with chloroform (175 mL) and the extract was washed with water and dried. Following the removal of solvent and unreacted 6-bromo-1-hexanol by distillation, the residue was purified by elution from a silica gel column using $CH_2Cl_2$:hexanes (9:1) as eluant to give 7-(3-methylisoxazol-5-yl)heptan-1-ol (26) (50%) as a yellow oil. IR (neat) 3610 $(OH)cm^{-1}$; NMR ($CDCl_3$) 1.12–1.96 (m, 10H, $(CH_2)_5$), 2.26 (S, 3H, Me-Het), 2.66 (t, J=9 Hz, 2H, $CH_2$—Het), 3.58 (t, J=9 Hz, 2H, $CH_2$—O), 5.84 (S, 1H, H-Het). Analysis found: C, 67.10; H, 9.79; N, 7.02. Required: C, 66.95; H, 9.71; N, 7.13 ($C_{11}H_{19}NO_2$)

Schematic for Example 26

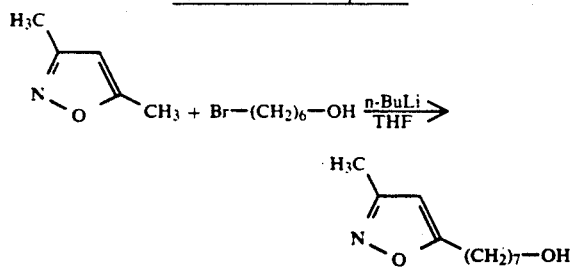

Following the same procedure as example 26, and starting with the appropriately substituted five-membered aromatic heterocycle, the following compounds were prepared.

EXAMPLE 27

6-(3,5-Dimethylpyrazol-1-yl)hexan-1-ol. (27)

Yellow oil (70%). IR (neat) 3590 $(OH)cm^{-1}$; NMR ($CDCl_3$) 1.10–1.95 (m, 8H, $(CH_2)_4$), 2.20 (S, 6H, Me-3, Me-5), 2.89 (S, 1H, OH), 3.49–4.10 (m, 4H, $CH_2$—N, $CH_2$—O), 5.72 (S, 1H, H-Het). Analysis found: C, 67.33; H, 10.32; N, 14.25. Required: C, 67.26; H, 10.26; N, 14.33 ($C_{11}H_{20}N_2O$).

EXAMPLE 28

7-(4-Methylthiazol-2-yl)heptan-1-ol. (28)

Yellow oil (50%). IR (neat) 3605 $(OH)cm^{-1}$; NMR ($CDCl_3$) 1.30–1.75 (m, 10H, $(CH_2)_5$), 2.40 (S, 3H, Me-Het), 2.95 (t, J=9 Hz, $CH_2$-Het), 3.60 (t, J=9 Hz, 2H, $CH_2$-O), 4.45 (S, 1H, H), 6.70 (S, 1H, H-Het). Analysis found: C, 62.03; H, 9.07; N, 6.47; S, 14.96. Required: C, 61.91; H, 8.97; N, 6.60; S, 15.02 ($C_{11}H_{19}NOS$).

EXAMPLE 29

6-(4-Methylthiazol-2-yl)thiohexan-1-ol. (29) (See the schematic representation of reaction given herebelow.

The mixture of 2-mercapto-4-methylthiazole (2.62 g, 0.02 mol), 6-bromo-1-hexanol (3.62 g, 0.02 mol), potassium carbonate (2.76 g, 0.02 mol) and acetone (50 mL) was refluxed for 14 h. After cooling, the mixture was filtered and the filtrate was evaporated. The residual oil was purified by elution from a silica gel column using ethylacetate-methanol (99:1, v./v) as eluant to give 6-(4-methylthiazol-2-yl)thiohexan-1-ol (29) (99%) as a yellowish oil. IR (neat) 3608 $(OH)cm^{-1}$; NMR ($CDCl_3$) 1.25–2.10 (m, 8H, $(CH_2)4$), 2.38 (S, 3H, Me-Het), 3.18 (t, J=9 Hz, 2H, $CH_2$—S), 3 65 (t, J=9 Hz, 2H, $CH_2$—O), 6.75 (S, 1H. H-Het). Analysis found: C, 51.98; H, 7.49; N, 5.92; S, 27.65. Required: C, 51.90; H, 7.40; N, 6.08; S, 27.71 ($C_{10}H_{17}NOS_2$).

Schematic for Example 29

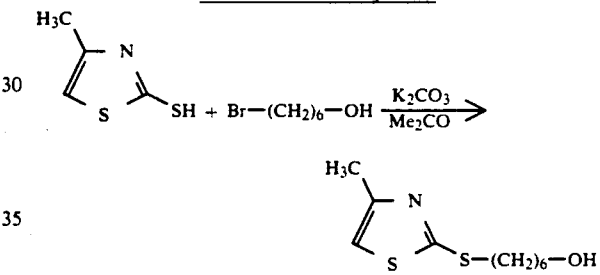

Calcium Channel Antagonist Testing

Calcium channel antagonist activity was determined as the concentration required to produce 50% inhibition of the muscarinic receptor-mediated $Ca^{+2}$-dependent contraction of guinea pig ileal longitudinal smooth muscle assay (C. Triggle, V. Swamy and D. Triggle, Can. J. Physiol. Pharmacol., 1979, 57, 804). Male albino guinea pigs (body weight 300–450 g) were sacrificed by decapitation. The intestine was removed above the ileo-caecal junction. Longitudinal smooth muscle segments of 2 cm length were mounted under a resting tension of 300–400 mg. The segments were maintained at 37° C. in a 10 ml jacketed organ bath containing oxygenated (100% $O_2$) physiological saline solution of the following composition (mM): NaCl: 137; $CaCl_2$: 2.6; KCl: 5.9; $MgCl_2$: 1.2; glucose: 11.9; buffered by Hepes-NaOH to pH 7.4. The muscles were equilibrated for 1 h with a solution change every 15 min. Two successive control contractions were elicited at 15 min. intervals with $5 \times 10^{-7}M$ carbachol. The isometric contractions were recorded with a force displacement transducer (FT 03C) on a GRASS* physiograph. The means of the three contractile responses was taken as the 100% value for the tonic (slow) component of the response. The muscle was washed with Hepes saline solution and was allowed to re-equilibrate. The calcium antagonist (test compound) was added ten min before the dose-response for carbachol was determined. The drug-induced inhibition of contraction was expressed as percent of control. The ID$_{50}$ values were graphically determined from the concentration-response curves, in triplicate. The test results are shown in Table I.

*Trademark

TABLE I

Calcium channel antagonist antihypertensive activity for the 3-(heteroarylalkyloxy-carbonyl)-5-methoxycarbonyl-2,6-dimethyl-4-(2 or 3-substitutedphenyl)-1,4-dihydropyridine derivatives tested.

| The Compound of Example No. | calcium channel antagonist act., inhib. act. on contractile response to CD ID$_{50}$(M) | |
| --- | --- | --- |
| 1 | 3.84 | 0.81 × 10$^{-9}$ |
| 3 | 5.13 | 1.09 × 10$^{-9}$ |
| 5 | 6.24 | 0.46 × 10$^{-9}$ |
| 11 | 3.25 | 0.33 × 10$^{-9}$ |
| 15 | 6.25 | 0.20 × 10$^{-9}$ |
| 18 | 5.48 | 0.74 × 10$^{-9}$ |
| 20 | 1.54 | 0.09 × 10$^{-8}$ |
| 19 | 5.81 | 0.13 × 10$^{-9}$ |
| 17 | 4.81 | 0.25 × 10$^{-8}$ |
| Nifedipine | 1.40 | 0.20 × 10$^{-8}$ |

The above-mentioned compounds did not show any negative ionotropic effect on heart muscle. Compound 11 has shown about 12% positive ionotropic effect on heart muscle with the same concentration as a smooth muscle relaxant (3.25×10$^{-9}$M). In the same condition, Compound 19 showed 25% positive ionotropic effect on heart muscle. Heart rate did not change in most of the cases. In SHR Rat, Compound 11 at a concentration of 0.2 mg/Kg showed a 19% drop in blood pressure for a period of 9h without changing the heart rate.

The in-vitro angiotensin inhibitory activity of certain compounds is shown in table II given herebelow.

TABLE II

| The Compound of Example No. | Concentration μg/ml | Percent Inhibition |
| --- | --- | --- |
| 1 | 0.01 | 93 |
| 5 | 0.01 | 95 |
| 13 | 0.1 | 80 |
| 15 | 0.1 | 64 |
| Captopril | 0.05 | 69 |

Captopril* which is the reference compound marketed by Squibb under the brand name Captoten, is known as an angiotensin converting enzyme inhibitor.
*Trademark The compound of example 1 at a concentration of 0.0025 μg still shows 60 percent inhibition. The compound of example 5 at a concentration of 0.001 μg shows 58 percent inhibition.

Table III given herebelow details the in-vivo (P.O.) anti-inflammatory activity of compounds 5 and 13 in comparison to commercially available compounds.

TABLE III

| The Compound of Example No. | Concentration mg/kg | Activity % |
| --- | --- | --- |
| 5 | 40 | 35 |
| 13 | 25 | 43 |
| Phenylbutazone* | 50 | 33 |
| Hydrocortisone | 25 | 32 |

Table IV given herebelow details the in-vivo (P.O.) anti-ulcer stress activity of compounds 1 and 15 in comparison to commercially available compounds.

TABLE IV

| The Compound of Example No. | Concentration mg/kg | Activity % |
| --- | --- | --- |
| 1 | 50 | 63 |
| 15 | 40 | 63 |
| Pirenzepine* | 50 | 75 |

*Trademark

The embodiments of the invention in which an exclusive property or privilege is claimed are defined as follows:

1. A 1,4-dihydropyridine derivative of the formula I:

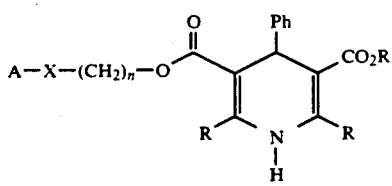

is provided in which:

A is an azole moiety selected from the group consisting of 3-methyl-5-isoxazolyl, 3,5-dimethyl-1-pyrazolyl and 4-methyl-2-thiazolyl;

R is a $C_1$-$C_4$ alkyl group;

X is —CH$_2$—, —S—, —SO— or —SO$_2$—;

n is 5, 6, 7 or 8; and

Ph is a phenyl group substituted once or twice by NO$_2$, CF$_3$ or Cl groups.

2. A 1,4-dihydropyridine derivative according to claim 1 of the formula II:

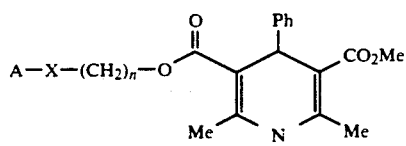

in which:

A is 3-methyl-5-isoxazolyl, 3,5-dimethyl-1-pyrazolyl, or 4-methyl-2-thiazolyl;

X is —CH$_2$—, —S—, —SO— or —SO$_2$—;

n is 5, 6, 7 or 8; and

Ph is a phenyl group substituted once or twice by NO$_2$, CF$_3$ or Cl groups.

3. A compound of claim 2 wherein A is 3-methyl-5-isoxazolyl.

4. A compound of claim 2 wherein A is 3,5-dimethyl-1-pyrazolyl.

5. A compound of claim 2 wherein A is 4-methyl-2-thiazolyl.

6. A compound of claim 2 wherein A is 3-methyl-5-isoxazolyl, X is CH$_2$, n is 6 and Ph is a phenyl group substituted once or twice by NO$_2$.

7. A compound of claim 2 wherein A is 3,5-dimethyl-1-pyrazolyl, X is CH$_2$, n is 6 and Ph is a phenyl group substituted once or twice by NO$_2$.

8. A compound of claim 2 wherein A is 4-methyl-2-thiazolyl, X is CH$_2$, n is 6 and Ph is a phenyl group substituted once or twice by NO$_2$.

9. A compound of claim 2 wherein A is 3-methyl-5-isoxazolyl, X is —SO$_2$—, n is 6 and Ph is a phenyl group substituted once or twice by NO$_2$.

10. A compound of claim 2 wherein A is 3,5-dimethyl-1-pyrazolyl, X is —SO$_2$—, n is 6 and Ph is a phenyl group substituted once or twice by NO$_2$.

11. A compound of claim 2 wherein A is 4-methyl-2-thiazolyl, X is —SO$_2$—, n is 6 and Ph is a phenyl group substituted once or twice by NO$_2$.

12. A compound of claim 2 wherein A is 3-methyl-5-isoxazolyl, X is —SO$_2$—, n is 6 and Ph is a phenyl group substituted once by CF$_3$.

13. A compound of claim 2 wherein A is 3,5-dimethyl-1-pyrazolyl, X is —SO$_2$—, n is 6 and Ph is a phenyl group substituted once by CF$_3$.

14. A compound of claim 2 wherein A is 4-methyl-2-thiazolyl, X is —SO$_2$—, n is 6 and Ph is a phenyl group substituted once by CF$_3$.

15. 3-[7-(3-methyl isoxazol-5-yl)heptyl-oxycarbonyl]-5-methoxycarbonyl-2,6-dimethyl-4-(3-nitrophenyl)-1,4-dihydropyridine, according to claim 1.

16. 3-[7-(3-methyl isoxazol-5-yl)heptyl-oxycarbonyl]-5-methoxycarbonyl-2,6-dimethyl-4-(2-nitrophenyl)-1,4-dihydropyridine, according to claim 1.

17. 3-[7-(3-methylisoxazol-5-yl)heptyl-oxycarbonyl]-5-methoxycarbonyl-2,6-dimethyl-4-(3-trifluoromethylphenyl)-1,4-dihydropyridine, according to claim 1.

18. 3-[7-(3-methylisoxazol-5-yl)heptyl-oxycarbonyl]-5-methoxycarbonyl-2,6-dimethyl-4-(2-trifluoromethylphenyl)-1,4-dihydropyridine, according to claim 1.

19. 3-[6-(3,5-dimethylpyrazol-1-yl)hexyloxycarbonyl]-5-methoxycarbonyl-2,6-dimethyl-4(3-nitrophenyl)-1,4-dihydropyridine, according to claim 1.

20. 3-[6-(3,5-dimethylpyrazol-1-yl)hexyloxycarbonyl]-5-methoxycarbonyl-2,6-dimethyl-4(2-nitrophenyl)-1,4-dihydropyridine, according to claim 1.

21. 3-[6-(3,5-dimethylpyrazol-1-yl)hexyloxycarbonyl]-5-methoxycarbonyl-2,6-dimethyl-4(3-trifluoromethylphenyl)-1,4-dihydropyridine, according to claim 1.

22. 3-[6-(3,5-dimethylpyrazol-1-yl)hexyloxycarbonyl]-5-methoxycarbonyl-2,6-dimethyl-4(2-trifluoromethylphenyl)-1,4-dihydropyridine, according to claim 1.

23. 3-[6-(3,5-dimethylpyrazol-1-yl)hexyloxycarbonyl]-5-methoxycarbonyl-2,6-dimethyl-4(3-chlorophenyl)-1,4-dihydropyridine, according to claim 1.

24. 3-[6-(3,5-dimethylpyrazol-1-yl)hexyloxycarbonyl]-5-methoxycarbonyl-2,6-dimethyl-4(2-chlorophenyl)-1,4-dihydropyridine, according to claim 1.

25. 3-17-(4-methylthiazol-2-yl)heptyloxycarbonyl]-5-methoxycarbonyl-2,6-dimethyl-4-(3-nitrophenyl)-1,4-dihydropyridine, according to claim 1.

26. 3-[7-(4-methylthiazol-2-yl)heptyloxycarbonyl]-5-methoxycarbonyl-2,6-dimethyl-4-(2-nitropheny1)-1,4-dihydropyridine, according to claim 1.

27. 3-[7-(4-methylthiazol-2-yl)heptyloxycarbonyl]-5-methoxycarbonyl-2,6-dimethyl-4-(3-trifluoromethylphenyl)-1,4-dihydropyridine, according to claim 1.

28. 3-[7-(4-methylthiazol-2-yl)heptyloxycarbonyl]-5-methoxycarbonyl-2,6-dimethyl-4-(2-trifluoromethylphenyl)-1,4-dihydropyridine, according to claim 1.

29. 3-[7-(4-methylthiazol-2-yl)heptyloxycarbonyl]-5-methoxycarbonyl-2,6-dimethyl-4-(3-chlorophenyl)-1,4-dihydropyridine, according to claim 1.

30. 3-[7-(4-methylthiazol-2-yl)heptyloxycarbonyl]-5-methoxycarbonyl-2,6-dimethyl-4-(2-chlorophenyl)-1,4-dihydropyridine, according to claim 1.

31. 3-[7-(4-methylthiazol-2-yl)heptyloxycarbonyl[-5-methoxycarbonyl-2,6-dimethyl-4-(2,3-dichlorophenyl)-1,4-dihydropyridine, according to claim 1.

32. 3-[6-(4-methylthiazol-2-yl)-thiohexyloxycarbonyl]-5-methoxycarbonyl-2,6-dimethyl-4-(3-nitrophenyl)-1,4-dihydropyridine, according to claim 1.

33. 3-[6-(4-methylthiazol-2-yl)-sulfoxyhexyloxycarbonyl]-5-methoxycarbonyl-2,6-dimethyl-4-(3-nitrophenyl)-1,4-dihydropyridine, according to claim 1.

34. 3-[6-(4-methylthiazol-2-yl)-sulfonylhexyloxycarbonyl]-5-methoxycarbonyl-2,6-dimethyl-4-(3-nitrophenyl)-1,4-dihydropyridine, according to claim 1.

35. A compound of claim 2 wherein A is 3-methyl-5-isoxazolyl, X is —S—, n is 6 and Ph is a phenyl group substituted once or twice by NO$_2$.

36. A compound of claim 2 wherein a is 3,5-dimethyl-1-pyrazolyl, X is —S—, n is 6 and Ph is a phenyl group substituted once or twice by NO$_2$.

37. A compound of claim 2 wherein A is 4-methyl-2-thiazolyl, X is —S—, n is 6 and Ph is a phenyl group substituted once or twice by NO$_2$.

38. A compound of claim 2 wherein A is 3-methyl-5-isoxazolyl, X is —S—, n is 6 and Ph is a phenyl group substituted once by CF$_3$.

39. A compound of claim 2 wherein A is 3,5-dimethyl-1-pyrazolyl, X is —S—, n is 6 and Ph is a phenyl group substituted once by CF$_3$.

40. A compound of claim 2 wherein A is 4-methyl-2-thiazolyl, X is —S—n is 6 and Ph is a phenyl group substituted once by CF$_3$.

41. A compound of claim 2 wherein A is 3-methyl-5-isoxazolyl, X is —SO—, n is 6 and Ph is a phenyl group substituted once or twice by NO$_2$.

42. A compound of claim 2 wherein A is 3,5-dimethyl-1-pyrazolyl, X is —SO—, n is 6 and Ph is a phenyl group substituted once or twice by NO$_2$.

43. A compound of claim 2 wherein A is 4-methyl-2-thiazolyl, X is —SO—, n is 6 and Ph is a phenyl group substituted once or twice by NO$_2$.

44. A compound of claim 2 wherein A is 3-methyl-5-isoxazolyl, X is —SO—, n is 6 and Ph is a phenyl group substituted once by CF$_3$.

45. A compound of claim 2 wherein A is 3,5-dimethyl-1-pyrazolyl, X is —SO—, n is 6 and Ph is a phenyl group substituted once by CF$_3$.

46. A compound of claim 2 wherein A is 4-methyl-2-thiazolyl, X is —SO—, n is 6 and Ph is a phenyl group substituted once by CF$_3$.

47. A compound of claim 2 wherein A is 4-methyl-2-thiazolyl, X is —SO— or —S—, n is 6 and Ph is a phenyl group substituted once or twice by a Cl group.

48. A compound of claim 2 wherein A is 3,5-dimethyl-1-pyrazolyl, X is —SO— or —S, n is 6 and Ph is a phenyl group substituted once or twice by a Cl group.

49. A compound of claim 2 wherein A is 3-methyl-5-isoxazolyl, X is —SO— or S, n is 6 and Ph is a phenyl group substituted once or twice by a Cl group.

50. A compound of claim 2 wherein A is 4-methylk-2-thiazolyl, X is —SO$_2$—, n is 6 and Ph is a phenyl group substituted once or twice by a CF$_3$ group, or a NO$_2$ group, or a Cl group.

51. A compound of claim 2 wherein A is 3,5-dimethyl-1-pyrazolyl, X is —SO$_2$—, n is 6 and Ph is a phenyl group substituted once or twice by a CF$_3$ group , or a NO$_2$ group or a Cl group.

52. A compound of claim 2 wherein A is 3-methyl-5-isoxazolyl, X is —SO$_2$—, n is 6 and Ph is a phenyl group substituted once or twice by a CF$_3$ group, or a NO$_2$ group or a Cl group.

53. A composition comprising a pharmaceutically effective amount of a compound of claim 1 and a pharmaceutically acceptable carrier.

54. A method of treating hypertension in a patient comprising administering an amount of a compound of claim 1 to a patient which is effective to reduce blood pressure.

55. A method of treating hypertension in a patient comprising administering an amount of the compound 3-[7-(3-methylisoxazol-5-yl)heptyloxycarbonyl]-5-methoxycarbonyl-2,6-dimethyl-4-(3-nitrophenyl)-1,4-dihydropyridine of claim 15 thereto which is effective to reduce blood pressure.

56. A method of treating hypertension in a patient comprising administering an amount of the compound 3-[6-(3,5-dimethylpyrazol-1-yl)hexyloxycarbonyl]-5-methoxycarbonyl-2, 6-dimethyl-4-(3-nitrophenyl)-1,4-dihydropyrdine of claim 19 thereto which is effective to reduce blood pressure.

57. A method of treating hypertension in a patient comprising administering an amount of the compound 3[7-(4-methylthiazol-2-yl)heptyloxycarbonyl]-5-methoxycarbonyl-2,6-dimethyl-4-(3-trifluoromethylphenyl)-1,4-dihydropyridine of claim 27 thereto which is effective to reduce blood pressure.

58. A method of treating hypertension in a patient comprising administering an amount of the compound 3-[7-(4-methylthiazol-2-yl)heptyloxycarbonyl]-5-methoxycarbonyl-2,6-dimethyl-4-(3-chlorophenyl)-1,4-dihydropyridine of claim 29 thereto which is effective to reduce blood pressure.

59. A method of treating inflammatory activity in a patient suffering from inflammation comprising administering a compound of claim 1 in an amount effective to reduce inflammation.

60. A method of treating ulcer stress activity in a patient suffering from ulcer stress comprising administering a compound of claim 1 in an amount effective to reduce ulcer stress.

61. A method of treating inflammatory activity which comprises administering the compound 3-[6-(3,5-dimethylpyrazol-1-yl)hexyloxycarbonyl]-5-methoxycarbonyl-2,6-dimethyl-4-(3-nitrophenyl)-1,4-dihydropyridine of claim 19 to a patient suffering from inflammation in an amount effective to reduce inflammation.

62. A method of treating inflammatory activity which comprises administering the compound 3-[7-(4-methylthiazol-2-yl)heptyloxycarbonyl]-5-methoxycarbonyl-2,6-dimethyl-4-(3-trifluoromethylphenyl)-1,4-dihydropyridine of claim 27 to a patient in an amount effective to reduce inflammation.

63. A method of treating ulcer stress activity in a patient which comprises administering 3-[7-(3-methylisoxazol-5-yl)heptylcarbonyl]-5-methoxycarbonyl-2,6-dimethyl-4-(3-nitrophenyl)-1,4-dihydropyridine thereto of claim 15 in an amount effective to reduce inflammation.

64. A method of treating ulcer stress activity in a patient which comprises administering 3-[7-(4-methylthiazol-2-yl)heptyl-oxycarbonyl]-5-methoxycarbonyl-2,6-dimethyl-4-(3-chlorophenyl)-1,4-dihydropyridine thereto of claim 29 in an amount effective to reduce inflammation.

65. The method of claim 54, wherein said compound is selected from the group consisting of 3-[7-(4-methylthiazol-2-yl)heptyloxycarbonyl]-5-methoxycarbonyl-2,6-dimethyl-4-(3-nitrophenyl)-1,4-dihydropyridine; 3-[7-(3-methylisoxazol-5-yl)heptyloxycarbonyl]-5-methoxycarbonyl-2,6-dimethyl-4-(3-trifluoromethylphenyl)-1,4-dihydropyridine; 3-[6-(3,5-dimethylpyrazol-1-yl)hexyloxycarbonyl]-5-methoxycarbonyl-2,6-dimethyl-4-(3-nitrophenyl)-1,4-dihydropyridine; 3-[7-(4-methylthiazol-2-yl)heptyloxycarbonyl]-5-methoxycarbonyl-2,6-dimethyl-4-(3-nitrophenyl)-1,4-dihydropyridine; 3-[7-(4-methylthiazol-2-yl)heptyloxycarbonyl]-5-methoxycarbonyl-2,6-dimethyl-4-(3-trifluoromethylphenyl)-1,4-dihydropyridine; 3-[7-(4-methylthiazol-2yl)heptyloxycarbonyl]-5-methoxycarbonyl-2,6-dimethyl-4-(3-chlorophenyl)-1,4-dihydropyridine; 3-[7-(4-methylthiazol-2-yl)heptyloxycarbonyl]-5-methoxycarbonyl-2,6-dimethyl-4-(2,3-dichlorophenyl)-1,4-dihydropyridine; 3-[6-(4-methylthiazol-2-yl)-thiohexyloxycarbonyl]-5-methoxycarbonyl-2,6-dimethyl-4-(3-nitrophenyl)-1,4-dihydropyridine; 3-[6-(4-methylthiazol-2-yl)-sulfoxyhexyloxycarbonyl]-5-methoxycarbonyl-2,6-dimethyl-4-(3-nitrophenyl)-1,4-dihydropyridine; and 3-[6-(4-methylthiazol-2-yl-sulfonylhexloxycarbonyl]-5-methoxycarbonyl-2,6-dimethyl-4-(3-nitrophenyl)-1,4-dihydropyridine.

* * * * *